United States Patent [19]

Kolb et al.

[11] Patent Number: 4,705,872

[45] Date of Patent: Nov. 10, 1987

[54] CYCLIC ACETAL-ALCOHOLS

[75] Inventors: Gerald C. Kolb, Bay City; Thomas W. Regulski, Midland, both of Mich.

[73] Assignee: The Dow Chemical Company, Midland, Mich.

[21] Appl. No.: 431,902

[22] Filed: Sep. 30, 1982

[51] Int. Cl.$^4$ ........................................... C07D 317/20
[52] U.S. Cl. ...................................... 549/448; 549/370
[58] Field of Search ................................ 549/370, 448

[56] References Cited

U.S. PATENT DOCUMENTS

| 3,208,993 | 9/1965 | Fischer et al. | 549/370 |
| 3,223,713 | 12/1965 | Kesslin et al. | 549/448 X |
| 3,514,435 | 5/1970 | Ardis et al. | 549/370 |
| 3,644,423 | 2/1972 | Roswell et al. | 549/448 |
| 3,708,502 | 1/1973 | Dunlop et al. | 549/370 |
| 3,739,017 | 6/1973 | Radly | 549/448 |
| 3,978,088 | 8/1976 | Renner et al. | 549/370 |
| 4,081,459 | 3/1978 | Mathais et al. | 549/370 |

FOREIGN PATENT DOCUMENTS

| 0746521 | 11/1966 | Canada | 549/370 |
| 0596586 | 3/1978 | U.S.S.R. | 549/370 |

Primary Examiner—Nicky Chan
Attorney, Agent, or Firm—Paul D. Hayhurst

[57] ABSTRACT

Novel cyclic diacetal-alcohols having cycloaliphatic bridging groups.

2 Claims, No Drawings

CYCLIC ACETAL-ALCOHOLS

BACKGROUND OF THE INVENTION

This invention relates to cyclic acetal-alcohols. More specifically, the invention relates to cyclic acetal-alcohols prepared by reacting cyclic dialdehydes with certain polyhydroxy compounds.

Phenylene-bridged cyclic diacetal-alcohols are described in U.S. Pat. No. 3,708,502. Heretofore, cyclic diacetal-alcohols having saturated cyclic bridging groups have not been disclosed.

SUMMARY OF THE INVENTION

The present invention is the discovery of cyclic diacetal-alcohols having saturated, cyclic radicals as bridging groups. These compounds are useful as cross-linking agents for polyisocyanates.

DETAILED DESCRIPTION OF THE INVENTION

In preparing a cyclic diacetal-alcohol of the present invention, a polyol is contacted with a dialdehyde in the presence of an acid. The polyols preferred for use in the present invention may be represented by the general formula:

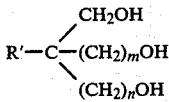

wherein m is zero or 1; n is an integer which is at least 1; and R' is hydrogen, alkyl or methylol. When R' is alkyl it is preferably alkyl of up to 2 carbon atoms. Preferably n is from 1 to about 4.

The cyclic dialdehydes of the present invention are non-aromatic, cyclic compounds which bear two aldehyde moieties. The preferred cyclic dialdehydes of the present invention may be represented by the formula:

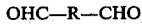

wherein R is a divalent, saturated, cyclic radical. Typical dialdehydes suitable for use in the present invention include cyclohexane dicarboxaldehyde, methyl cyclohexane dicarboxaldehyde, tetrahydropyran dicarboxaldehyde, norbornane dicarboxaldehyde, and octahydro-4,7-methano-indene dicarboxaldehyde. Preferred dialdehydes are cyclohexane dicarboxaldehyde, methyl cyclohexane dicarboxaldehyde, and norbornane dicarboxaldehyde.

The amounts of the reactants employed are not critical. Some of the desired product is obtained when any amount is employed. However, the reaction consumes the reactants in the molar ratio of 2 moles of polyol to one mole of dialdehyde, and the use of such amounts is preferred.

The reaction of the dialdehyde and the polyol is catalyzed by acid. Typical acids suitable for use include strong mineral acids, and strong inorganic or organic acids. Examples of suitable acids include hydrochloric, sulfuric, phosphoric, oxalic, dichloroacetic, trichloroacetic, and para-toluenesulfonic acid. The preferred acid catalyst is para-toluenesulfonic acid. The acid is employed in a catalytic amount. Typically from about 0.001 to about 0.005 or more moles of acid are employed per mole of dialdehyde.

The reaction is conveniently and preferably carried out in an inert liquid reaction medium which is a solvent for at least one of the reactants, and which is typically an organic liquid. Suitable inert liquids include water and hydrocarbons such as hexane, benzene and toluene. Chloroform is a preferred inert liquid reaction medium. The reaction may also be conducted neat or in the polyol as a liquid at the reaction temperature. The amount of inert liquid reaction medium to be employed is indicated by practical considerations, but typically can be any amount which is sufficient to solubilize the reactants. Preferably, from about 1 to about 3 liters of inert liquid reaction medium is employed per mole of dialdehyde.

The reaction proceeds at temperatures ranging from about 25° C. to about 200° C. Conveniently, the reaction is conducted at reflux temperature when the boiling temperature of the liquid employed as the reaction medium is in the aforementioned temperature range. The preferred temperature range is between about 40° C. and 125° C. Ordinarily, the reaction will proceed readily at atmospheric pressure or higher, but subatmospheric pressures may be employed if desired.

When the reactants and the catalyst are combined under the conditions described hereinbefore, a cyclic acetal-alcohol is produced. The preferred cyclic acetal-alcohols of the present invention may be represented by the formula:

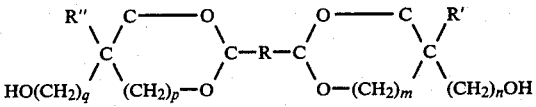

wherein n, m, R and R' are as previously described; p is zero or 1; q is an integer which is at least 1; and R" fits the description of R' and may be identical or nonidentical to R'. Most preferably, q and n are independently from 1 to about 4.

SPECIFIC EMBODIMENTS

The following examples are given to illustrate the invention, but these examples should not be construed as limiting its scope. All parts and percentages are by weight unless otherwise indicated.

EXAMPLE 1

To a 500-ml 3-neck flask equipped with a Dean-Stark trap, a stirring means, a heating means and a condensing means, is charged 18.4 g (0.20 mole) glycerin, 14.0 g (0.10 mole) cyclohexane dicarboxaldehyde, 0.10 g p-toluenesulfonic acid monohydrate and 250 ml chloroform. The reaction mixture is heated to reflux (60° C. to 65° C.) with stirring until no further water is collected in the Dean-Stark trap. The resulting reaction mixture is cooled to room temperature and then is poured into a dilute sodium bicarbonate solution, is washed with water and then with a concentrated sodium chloride solution. The organic layer is separated and dried over magnesium sulfate, is filtered, and the solvent is removed under reduced pressure using a rotary evaporator. A yield of 26.8 g, which is 92.0 percent of the theoretical yield, of a clear, viscous liquid is obtained. The cyclic diacetal-alcohol structure is confirmed by infrared and nuclear magnetic resonance (NMR) analyses.

EXAMPLE 2

Using the equipment of Example 1, 37.0 g (0.40 mole) glycerin, 30.5 g (0.20 mole) norbornane dicarboxaldehyde, 0.10 g p-toluenesulfonic acid monohydrate and 200 ml chloroform are heated with stirring to reflux temperature and are held at reflux until no further water is collected in the Dean-Stark trap. A total of 7.2 g of water is collected over a period of 1 hour. The mixture is cooled to room temperature, and then is post-treated using the post-treatment method of Example 1. A yield of 56.5 g, which is 93.7 percent of the theoretical yield, of a clear viscous liquid is obtained. Infrared and NMR analyses confirm the structure of the cyclic diacetal-alcohol product.

Comparative Experiment 1 —Not an embodiment of the present invention

Using the equipment of Example 1, 13.4 g (0.10 mole) terephthalaldehyde, 18.4 g (0.20 mole) glycerin, 0.10 g p-toluenesulfonic acid monohydrate and 250 ml chloroform is heated with stirring at reflux temperature for 2 hours. The amount of water in the Dean-Stark trap is 2.5 ml. A fine white precipitate starts coming out of solution after 1 hour of reaction time. The reaction mixture is cooled to room temperature and the precipitate is filtered and vacuum dried. A crude yield of 25.0 g, which is 88.7 percent of the theoretical yield, is obtained. The crude product is recrystallized from a solution of ethanol and water. Infrared and NMR analyses confirm the structure of the aromatic-bridged cyclic diacetal-alcohol.

EXAMPLE 3

The procedure of Example 2 is repeated except that a molar equivalent of 1,2,6-hexanetriol is used instead of glycerin. A yield of 36.6 g, which is 98.4 percent of the theoretical yield, of a light yellow viscous liquid is obtained.

EXAMPLE 4

The procedure of Example 1 is repeated except that a molar equivalent of 1,1,1-tris(hydroxymethyl)-ethane was used instead of glycérin. A yield of 34.2 g, which is 99.0 percent of the theoretical yield, of a white, waxy solid is obtained.

EXAMPLE 5

The procedure of Example 1 is repeated except that a molar equivalent of methyl cyclohexane dicarboxaldehyde is used instead of cyclohexane dicarboxaldehyde. A yield of 30.0 g of a clear yellow viscous liquid is obtained.

EXAMPLE 6

A blocked isocyanate acrylate polymer is solution polymerized using the formulation:
31.2 parts 2-isocyanato-ethyl-methacrylate blocked with methyl ethyl ketoxime;
34.4 parts methyl methacrylate;
34.4 parts ethyl acrylate; and
1.5 parts Vazo 52 (an initiator available from E.I. du Pont de Nemours & Co.). The polymer has the following characteristics, as determined by gel permeation chromatographic analysis using a polystyrene standard:
$\overline{M}_n = 16,300$
$\overline{M}_w = 35,900$
$\overline{M}_w \overline{M}_n = 2.2$ Twenty grams of a 50.0 percent by weight solution containing the blocked isocyanate acrylate polymer and Cellosolve acetate (an ethylene glycol monoethyl ether acetate available from Union Carbide Corporation) is added to a 4-ounce wide-mouth bottle. Dibutyltin diacetate (0.05 g) is added to the solution and the jar is placed on a mechanical shaker for approximately 10 minutes. To a different 4-ounce jar is added 2.4 g (6.45 mmoles) of the product of Example 3 and 5.0 g of Cellosolve acetate. This jar is placed on a mechanical shaker for approximately 10 minutes. Then the solution containing the product of Example 3 is added to the isocyanate-containing solution and the mixture is shaken on a mechanical shaker for approximately 10 minutes to produce a polymer solution. The polymer solution is spread with a wound wire rod onto steel test panels, which have been treated with zinc phosphate and rinsed with acetone, to form coatings. The coatings are air dried for 10 minutes, and are then cured at 150° C. for 30 minutes. The coatings are observed to have excellent gloss, adhesion and solvent resistance to methyl ethyl ketone. The physical properties of these coatings are summarized in Table I.

EXAMPLE 7

Coatings are made according to the method described in Example 6 except that the polymer is unblocked and with the exception that the coatings are cured at 85° C. The physical properties are summarized in Table I. The coatings were observed to have excellent gloss and adhesion and resistance to methyl ethyl ketone.

Comparative Experiment 2 —Not an embodiment of the present invention

Coatings are made using the method of Example 6 with the exception that 1.8 g of the acetal-alcohol of Comparative Experiment 1 are shaken with 10.0 g of Cellosolve acetate. The resulting coatings are very rough in appearance and lack the high gloss typically found for the cyclic acetal-alcohols of the present invention. The physical properties of these coatings are summarized in Table I.

EXAMPLE 8

Coatings are prepared using the method of Example 6 except that 1.95 g (0.0129 mole) of the acetal-alcohol of Example 5 is used as the cross-linking agent. The physical properties of the coatings are summarized in Table I.

EXAMPLE 9

Coatings are prepared using the method of Example 6 except that 1.8 g (0.0120 mole) of the acetal-alcohol of Example 2 is dissolved in 8 g of ethyl acetate. The physical properties of the coatings are summarized in Table I.

TABLE I

Physical Properties of the Cured Coatings

| Coating of Example | Percent Gloss 20° | Percent Gloss 60° | Percent Adhesion | Pencil Hardness | Resistance to Methylethyl Ketone | Impact RI (Thickness) DI | | Cure Temp. |
|---|---|---|---|---|---|---|---|---|
| 6 | 77 | 91 | 100 | H-2H | >100DR | >30 (1.7-1.9 mils) | 30 | 150 |
| 7 | 76 | 89 | 100 | H-2H | >25DR[1] | 25 (2.7-2.8 mils) | 30 | 85 |
| CE2 | 23 | 49 | 97 | H-2H | — | — | | 150 |
| 8 | 79 | 90 | 100 | 2H-3H | >100DR | 2 (2.1-2.3 mils) | 30 | 150 |
| 9 | 84 | 96 | 100 | 2H-3H | >100DR | 2 (0.8-1.1 mils) | 30 | 150 |

[1]This coating not tested beyond 25 DR, but the coating is not worn through.

The novel cyclic acetal-alcohols of the present invention provide a means of cross-linking polyisocyanates formulated using conventional paint solvents to yield cured coatings having improved adhesion, gloss, hardness, solvent resistance and other improved physical properties.

Testing Methods

The testing methods used to obtain the foregoing data are described as follows:

Gloss:

The gloss of a cured coating is measured using a Gardner brand Multigloss meter which is calibrated after each reading using ASTM standardized tile panels. At least two readings are taken for each angle, and the average of the readings is recorded for each angle as the percent gloss at the given angle of reflectance.

Percent Adhesion:

A 10 by 10 crosshatch having an area of one square inch is inscribed into a cured coating using a razor. Scotch brand #600 tape is placed on the crosshatched area. The tape is then pulled directly upward perpendicular to the coating. The percent adhesion is recorded as the number of crosshatched squares which remain attached to the panel.

Pencil Hardness:

Pencils of varying hardness (H, 2H, 3H) are sharpened and then filed down to a flat point using fine emery paper. A pencil is then held at a 45° angle and is moved along a cured coating in a line for a distance of about 1" under moderate pressure. The coating is examined for scratches; if a scratch occurs the test is repeated using a pencil which is one grade softer and the coating is examined for scratches. The procedure is repeated until no scratching of the coating is observed. If no scratch is observed with the first pencil, then the procedure is repeated using successively harder pencils. Two values are recorded. The first value is the hardness of the hardest pencil which may be used without scratching the coating. The second value is the hardness of the softest pencil which will scratch the coating.

Resistance to Methyl Ethyl Ketone:

A ball-peen hammer with a mass of 1088 g is wrapped with 8 thicknesses of cheesecloth on the peen end. The cheesecloth is saturated with methyl ethyl ketone. The peen end of the hammer head is then dragged back and forth over the cured coating; each back and forth cycle is called a double rub. The number of double rubs is recorded when the coating is rubbed off of the panel or when 100 double rubs have occurred before the coating wears through.

Reverse and Direct Impact:

A Gardner brand impact tester having a ½" diameter steel-nosed projectile having a mass of 915 g is used. The projectile is dropped from increasing heights onto the uncoated (reverse) or coated (direct) side of a 24 gauge test panel, and the coating is examined after each impact for splits or cracks. The product of the mass and height for the highest impact which a coating survives is recorded, after conversion to inch-pounds, as the reverse (RI) or direct (DI) impact. The RI and DI are dependent on the thickness of each coating, so the thickness of a coating is measured and recorded in parentheses.

As previously mentioned, the preceding examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A cyclic acetal-alcohol of the formula:

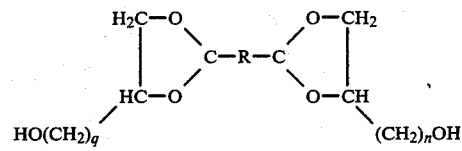

wherein R is cyclohexylene, methylcyclohexylene, or norbornylene; and n and q are independently at least 1.

2. A cyclic acetal-alcohol of the formula:

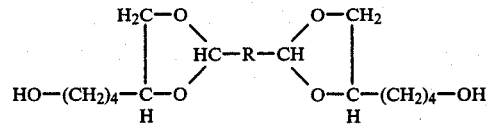

wherein R is norbornylene

* * * * *